United States Patent [19]
Shih

[11] Patent Number: 5,133,839
[45] Date of Patent: Jul. 28, 1992

[54] LOWER ALKYLENE OXIDE PURIFICATION

[75] Inventor: T. Thomas Shih, Bryn Mawr, Pa.

[73] Assignee: Arco Chemical Technology, L.P., Wilmington, Del.

[21] Appl. No.: 735,574

[22] Filed: Jul. 25, 1991

[51] Int. Cl.⁵ .................... B01D 3/40; C07D 301/32
[52] U.S. Cl. ........................................ 203/64; 203/70; 203/75; 203/80; 203/DIG. 19; 549/541
[58] Field of Search ............... 203/64, 70, DIG. 19, 203/81, 82, 74, 75, 80; 549/541, 542

[56]     References Cited
U.S. PATENT DOCUMENTS

| | | | |
|---|---|---|---|
| 3,338,800 | 8/1967 | Binning et al. | 549/541 |
| 3,464,897 | 9/1969 | Jubin | 549/541 |
| 3,578,568 | 5/1971 | Washall | 549/541 |
| 3,632,482 | 1/1972 | Hoory et al. | 203/56 |
| 3,843,488 | 10/1974 | Schmidt et al. | 549/541 |
| 3,881,996 | 5/1975 | Schmidt | 549/541 |
| 4,402,794 | 9/1983 | Nemet-Mavrodin et al. | 549/541 |
| 5,000,825 | 3/1991 | Shih | 549/541 |

FOREIGN PATENT DOCUMENTS 2108922  8/1972  Fed. Rep. of Germany ...... 549/542

Primary Examiner—Wilbur Bascomb, Jr.
Attorney, Agent, or Firm—William C. Long

[57]     ABSTRACT

The present invention provides an improved process for the separation of impurities from a lower alkylene oxide, such as propylene oxide, by a process wherein the impure propylene oxide is first fractionally distilled to separate higher and lower boiling impurities, then the partially purified alkylene oxide is subjected to extractive distillation to separate additional impurities, the purified propylene oxide being separated as an overhead fraction.

4 Claims, 2 Drawing Sheets

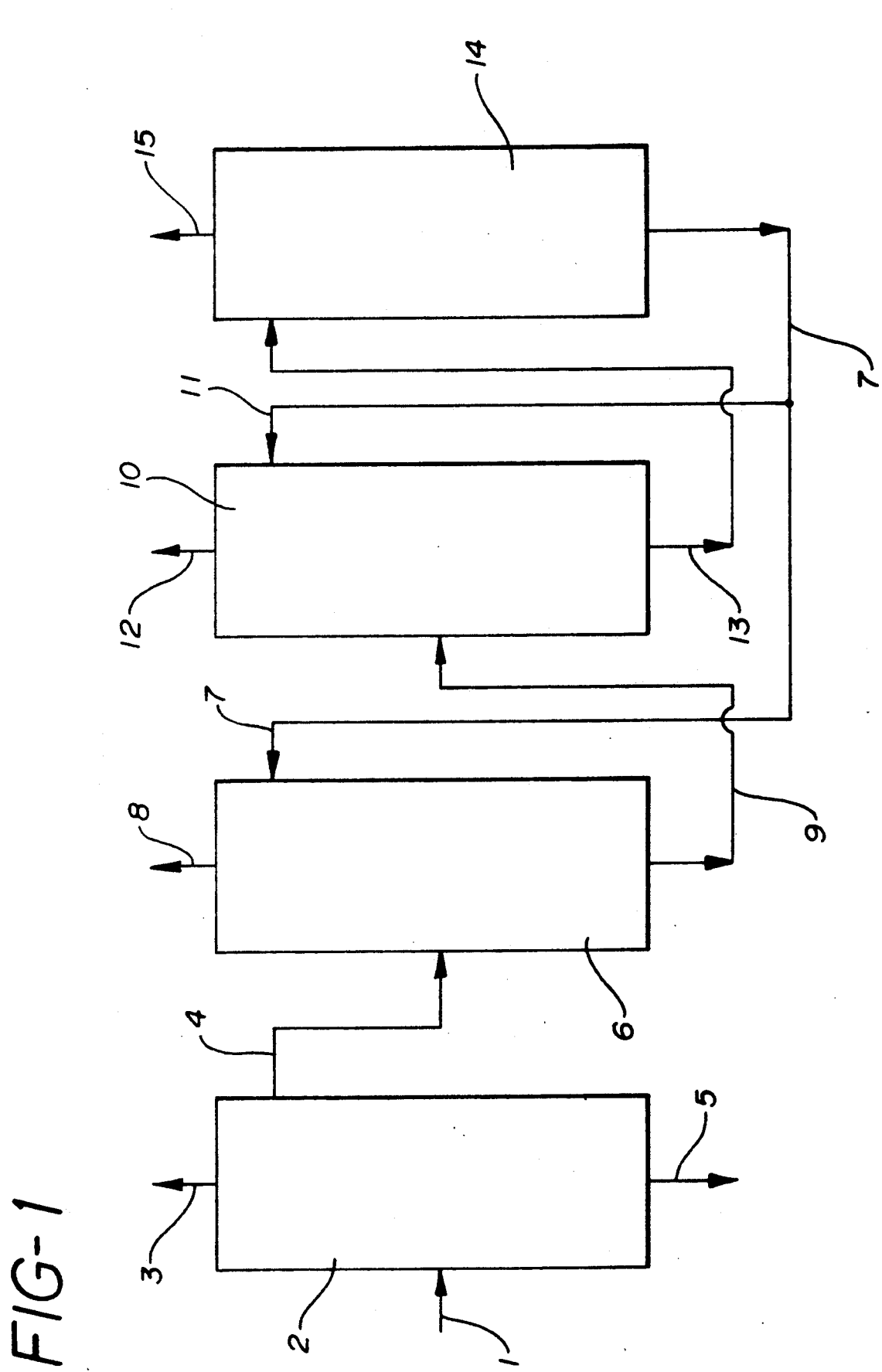

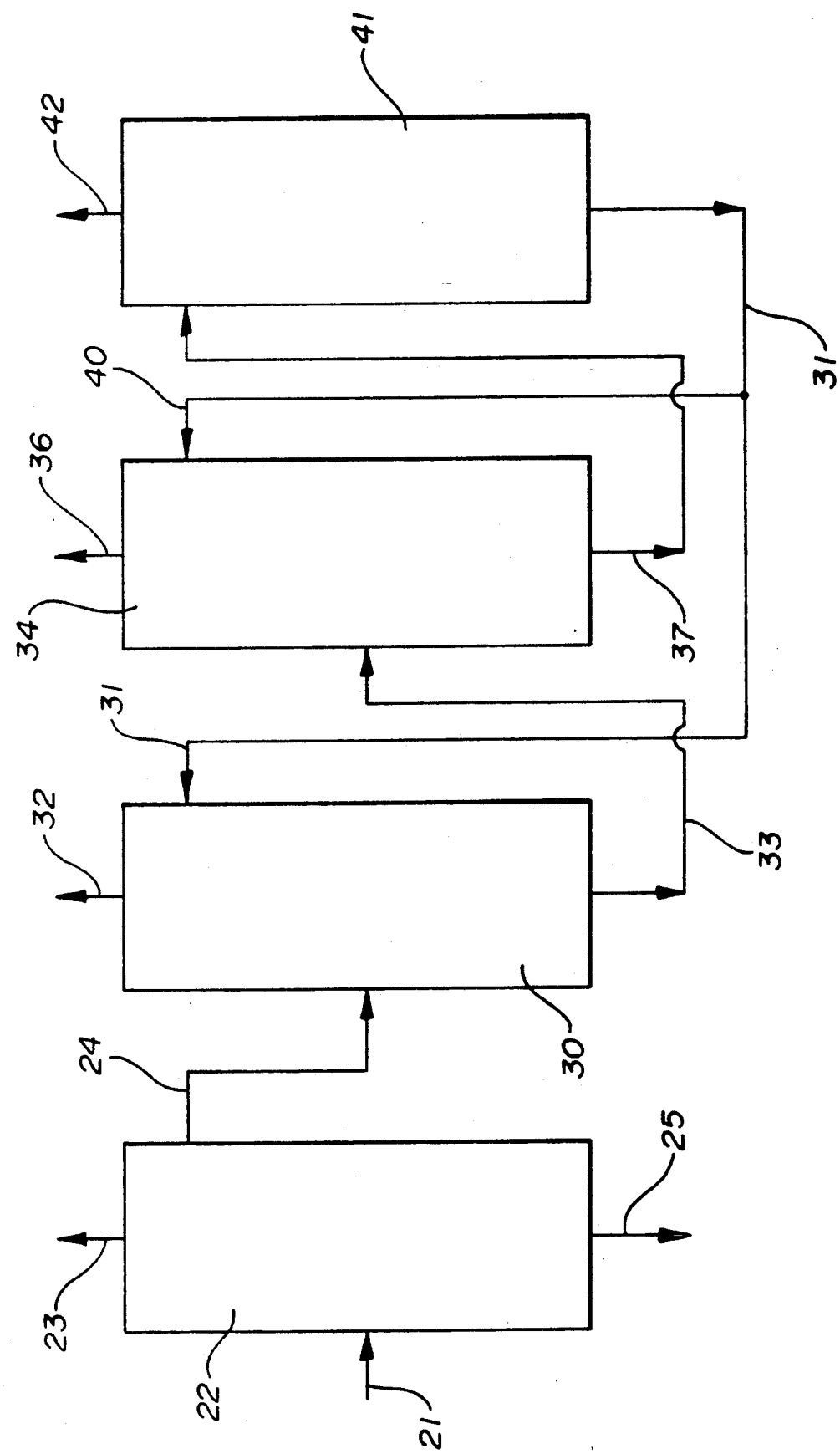

LOWER ALKYLENE OXIDE PURIFICATION

BACKGROUND OF THE INVENTION

1. Field of the Invention

The present invention relates to the separation of hydrocarbon and oxygenated compound impurities from lower alkylene oxides such as propylene oxide by an improved sequence of conventional and extractive distillation.

2. Description of the Prior Art

Monoepoxides such as propylene oxide are highly important chemicals useful in a great number of applications. An important commercial technology for producing the monoepoxides is via the catalytic reaction between the corresponding olefin and an organic hydroperoxide. See, for example, U.S. Pat. No. 3,351,635.

From the epoxidation reaction mixture, a crude monoepoxide product can be recovered by conventional distillation. The type and quantity of impurities associated with the crude monoepoxide will depend to a considerable extent on the organic hydroperoxide used in the reaction to form the monoepoxide Where ethylbenzene hydroperoxide is used in the epoxidation reaction, for example, the crude monoepoxide will contain such heavy contaminants as phenol, ethyl benzene, methyl benzyl alcohol and acetophenone which are not found in monoepoxide formed by reaction of tertiary butyl hydroperoxide with the same olefin. In the latter case, tertiary butyl alcohol is present as a contaminant in the crude monoepoxide.

Certain impurities are common to crude monoepoxide prepared by both of the above reactions; these include methanol, methyl formate, propionaldehyde and acetone. However the amounts of such impurities present with the crude monoepoxide differs very greatly depending upon the reaction by which the monoepoxide is formed, and the monoepoxide purification procedure used to recover purified monoepoxide have differed very greatly.

In the case of monoepoxide prepared as a result of reaction of lower olefin with ethylbenzene hydroperoxide, the crude monoepoxide is first subjected to conventional distillation in order to remove the higher boiling components ethyl benzene, methyl benzyl alcohol and acetophenone as well as some of the oxygenated impurities before passing to extractive distillation for final purification.

In the case of monoepoxide containing none of the heavies listed above and containing much greater amounts of the oxygenated impurities is first subjected to one or more extractive distillation steps to remove oxygenated impurities before undergoing a conventional distillation step to recover the purified monoepoxide.

A disadvantage of the prior procedures used in the purification of monoepoxide from reaction of olefin with tertiary butyl hydroperoxide has been the large amounts of extractive distillation solvent and, consequently, the utilities used In addition, in the prior procedures, there tended to be formed significant amounts of polymers of the monoepoxide which necessitated an additional carbon treatment step as described in U.S. Pat. No. 4,692,535.

The present invention provides an improved sequence of conventional and extractive distillations steps for the purification of crude monoepoxide formed by reaction of olefin with tertiary butyl hydroperoxide and containing by weight at least 1500 ppm methanol, at least 100 ppm methyl formate, at least 150 ppm propionaldehyde, at least 3000 ppm acetone and up to 1000 ppm tertiary butyl alcohol.

Prior workers have provided extractive distillation techniques to accomplish the separation of impurities from monoepoxides such as propylene oxide U S. Pat. No. 3,838,020 shows a dual solvent extractive distillation process. U.S. Pat. No. 3,843,488 shows extraction distillation using a $C_8$ to $C_{20}$ hydrocarbon to purify propylene oxide U S. Pat. No. 3,909,366 shows extractive distillation purification of propylene oxide using $C_6$ to $C_{12}$ aromatic hydrocarbon. U.S. Pat. No. 4,140,588 uses water in extractive distillation purification of propylene oxide. U.S. Pat. No. 3,881,996 uses plural stage distillation to purify propylene oxide. East German Patent Specification uses aliphatic alcohols such as tertiary butanol in separating methyl formate from propylene oxide by extractive distillation. U.S. Pat. No. 5,006,206 uses tertiary butyl alcohol and water in the extractive distillation purification of propylene oxide.

It has previously been proposed to separate oxygen containing impurities from the propylene oxide by extractive distillation using lower glycols such as ethylene glycol and propylene glycol. See U.S. Pat. No. 3,578,568 which describes this procedure and which teaches use of solvent in amount to comprise 15 to 50% of the vapor space in the distillation zone. U.S. Pat. No. 5,000,825 describes a similar separation but one which uses much lower solvent concentrations whereby propylene oxide losses are reduced.

U.S. Pat. No. 3,477,919 teaches a method for purifying propylene oxide contaminated with impurities such as methyl formate which boil near propylene oxide. The methyl formate impurity is removed from the contaminated propylene oxide by reaction with an aqueous slurry of calcium hydroxide.

U.S. Pat. No. 2,622,060 teaches a process for separating propylene oxide from a crude reaction mixture by treatment with an aqueous alkali metal hydroxide solution.

U.S. Pat. No. 2,550,847 teaches a process for the purification of propylene oxide in a crude reaction mixture containing methyl formate by subjecting the mixture to strong agitation with an aqueous solution of an alkaline saponifying agent.

U.S. Pat. No. 3,350,417 teaches a process for purifying propylene oxide comprising parallel and serial stages of distillation and a caustic treatment to simultaneously aldolize acetaldehyde and saponify methyl formate. The solvent used in the reaction step is removed before subsequent caustic treatment.

U.S. Pat. No. 4,691,034 removes methyl formate from propylene oxide by contact with an aqueous calcium hydroxide slurry to which a solubilizer has been added. U.S. Pat. No. 4,691,035 removes methyl formate from propylene oxide by contact with a base such as sodium hydroxide in water and glycerol.

U S. Pat. No. 4,692,535 shows the removal of high molecular weight ethers from propylene oxide by treatment with an absorbent such as activated carbon.

Although a great deal of work has been done as above indicated with regard to lower alkylene oxide purification, there still exists considerable room for improvement in both the efficiency of the purification and in the quality of the product alkylene oxide.

BRIEF DESCRIPTION OF THE INVENTION

In accordance with the present invention, it has been found that crude lower alkylene oxides having 2 to 4 carbon atoms, particularly propylene oxide, formed by reaction of olefin with tertiary butyl hydroperoxide, and containing by weight at least 1500 ppm methanol, at least 100 ppm methyl formate, at least 150 ppm propionaldehyde, at least 3000 ppm acetone and up to 1000 ppm tertiary butyl alcohol can be purified by an improved sequence of conventional and extractive distillation steps.

BRIEF DESCRIPTION OF THE DRAWINGS

FIG. 1 illustrates in schematic form an embodiment of the invention.

FIG. 2 illustrates in schematic form an alternate embodiment.

DETAILED DESCRIPTION OF THE INVENTION

This invention is applicable to the purification of crude alkylene oxide having 2 to 4 carbon atoms, especially prepared by reaction of tertiary butyl hydroperoxide with the corresponding olefin and containing the contaminants designated above.

The invention can be described by reference to FIG. 1 which illustrates a specific practice of the invention, with particular reference to the purification of propylene oxide, in schematic form using an extractive distillation agent such as octane. Referring to FIG. 1, impure lower alkylene oxide, illustratively crude propylene oxide, produced by the reaction of propylene and tertiary butyl hydroperoxide, is introduced via line 1 into conventional distillation zone 2. The impure propylene oxide contains impurities which are customarily formed during the manufacture procedure, i.e. at least 1500 ppm methanol, at least 100 ppm methyl formate, at least 150 ppm propionaldehyde, at least 3000 ppm acetone and up to 1000 ppm tertiary butyl alcohol. Distillation zone 2, although depicted as a single, conventional distillation zone, preferably, in actuality comprises at least two conventional distillation zones each adapted to separate an overhead and a bottoms distillation stream. Distillation zone 2 is operated in a conventional fashion, and in this zone light impurities including formaldehyde, methyl formate, acetaldehyde and light hydrocarbons are separated as an overhead distillate stream via line 3. In addition, in distillation zone 2 there is accomplished the separation of heavier impurities, that is impurities which are higher boiling than propylene oxide, via bottoms stream 5. These impurities are methanol, acetone, propionaldehyde and water. An advantage of operating the conventional distillation as the first purification step is that the bulk of the above named impurities can be separated from propylene oxide by conventional distillation procedures without the expense associated with provision of extractive distillation procedures.

An intermediate boiling propylene oxide stream, greatly reduced in the content of impurities, is removed from zone 2 via line 4 and passes to extractive distillation zone 6. In zone 6 an extractive distillation solvent, most preferably octane, is introduced via line 7 and effectively increases the volatility of various impurities relative to propylene oxide so that these materials including methyl formate, methanol and water, can readily be removed overhead via line 8. The further purified propylene oxide in admixture with the extractive distillation solvent is separated via line 9 and passes to a second extractive distillation zone 10 wherein extractive distillation solvent, again preferably octane, is introduced via line 11, and the extractive distillation is carried out in zone 10 with the purified, high quality propylene oxide product removed overhead via line 12. The extractive solvent, containing various impurities, is removed via line 13 and passes to stripper 14 wherein the impurities are stripped and purged as overhead via line 15. The stripped solvent passes via lines 11 and 7 back to the extractive distillation zones for further use in the process.

A significant advantage of the procedure described above is that the propylene oxide product stream is removed as an overhead distillate from extractive distillation zone 10. This is in contrast to prior procedures where the product propylene oxide was removed as a side stream from the appropriate distillation column. In prior procedures there tended to be acid catalyzed condensation of propylene when removed as a side stream distillate, thus requiring a further treatment step, such as carbon adsorption, in order to remove the condensed propylene oxide impurities.

An alternative embodiment of the invention is shown in FIG. 2 in which an extractive distillation solvent is used, such as a lower alkylene glycol, which decreases the volatility of various impurities relative to propylene oxide. Referring to FIG. 2, the impure propylene oxide is subjected to conventional distillation in zone 22 such as was described above in connection with zone 2. The light impurities are removed overhead via line 23 and the heavy impurities via line 25.

An intermediate boiling propylene oxide stream, greatly reduced in the content of impurities, is removed from zone 22 via line 24 and passes to extractive distillation zone 30. In zone 30 an extractive distillation solvent, most preferably propylene glycol, is introduced via line 31 and effectively increases the volatility of hydrocarbon impurities relative to propylene oxide so that these materials can readily be removed overhead via line 32.

The propylene oxide and solvent mixture is removed from zone 30 via line 33 and passes to extractive distillation zone 34. Additional propylene glycol extractive distillation solvent is introduced into zone 34 via line 40. From zone 34 a purified propylene oxide product is removed overhead by means of line 35. A bottoms stream comprised of solvent glycol and impurities is removed via line 37 and passes to distillation zone 41. In zone 41, an overhead stream containing water, methanol and the like is separated and removed via line 42. The purified solvent is returned via lines 31 and 40 for reuse in the process.

A significant advantage of the procedures set forth above resides in the fact that the quality of the product propylene oxide is substantially superior to that which is produced by present procedures. A further advantage is that more efficient use of the extractive distillation system is accomplished. By removing a predominance of the higher and lower boiling impurities in the first conventional distillation column, solvent requirements in the subsequent impurities removal by extractive distillation are significantly reduced as are the process utilities requirement.

The particular conditions of the conventional and extractive distillations steps are not per se novel. Generally, the conventional distillation involves use of a column having at least 20 theoretical stages. Illustrative overhead temperatures and pressures are 45° to 65° C. and 25 to 35 psia. Illustration bottoms temperatures and pressures are 60° to 75° C. and 35 to 45 psia.

Extractive distillation procedures known in the art can be employed. Especially preferred in the process of FIG. 1 is the use of $C_8$ to $C_{20}$ alkane extractive distillation solvents, particularly octane, as taught in U.S. Pat. No. 3,843,488, and aromatic solvents as taught in U.S. Pat. No. 3,909,366. The procedures described in U.S. Pat. Nos. 3,578,568 and 5,000,825 using lower alkylene glycol extractive distillation solvents are especially useful in the process of FIG. 2.

The invention can now be illustrated by reference to a working example in conjunction with FIG. 1 accompanying this specification. Referring to FIG. 1, a crude propylene oxide product by reaction of propylene with tertiary butyl hydroperoxide is purified in accordance with the invention. The crude propylene oxide entering distillation zone 2 via line 1 contains 275 ppm methyl formate, 50 ppm formaldehyde, 210 ppm acetaldehyde, 850 ppm hydrocarbon impurities, 2000 ppm methanol, 5000 ppm acetone, 150 ppm propionaldehyde and 3800 ppm water. The crude propylene oxide enters zone 2 at a rate of 2000 lbs./hr. and therein is subjected to a conventional fractional distillation. Zone 2 has 35 theoretical stages and is operated at an overhead temperature and pressure of 56° C. and 29 psia and a bottoms temperature and pressure of 68° C. and 38 psia. About 40 lbs./hr. of a lower boiling impurities stream comprising 0.009 lbs./hr. formaldehyde, 0.33 lbs./hr. methyl formate, 0.273 lbs./hr acetaldehyde, 0.17 lbs./hr $C_5$ hydrocarbon impurities is removed via line 3. Heavier impurities comprised of 3.0 lbs. methanol, 9.8 lbs. acetone, 0.0285 lbs. propionaldehyde and 6.46 lbs. water and 0.16 lbs. $C_7$ hydrocarbons are separated via line 5.

The partially purified propylene oxide passes via line 4 to extractive distillation zone 6 wherein the impure propylene oxide is extractively distilled using octane as extractive distillation solvent. Octane in amount of 10000 lbs./hr. is passed from stripper 14 via line 7 to extractive distillation column 6. The column comprises 45 theoretical stages and is operated at an overhead temperature and pressure of 40° C. and 18 psia. Impurities comprised of 0.198 lbs./hr. methyl formate, 0.96 lbs./hr. methanol and 0.96 lbs./hr. water are removed via line 8. The purified propylene oxide and solvent are removed via line 9 and pass to further extractive distillation zone 10. Bottoms distillation conditions in zone 6 are 94° C. and 28 psia.

Additional extractive distillation solvent, preferably octane, is introduced at the rate of 10000 lbs./hr. into zone 10 by means of line 11. In extractive distillation zone 10 the relative volatilities are such that propylene oxide is removed overhead via line 12 at the rate of 1920 lbs./hr. Overhead conditions in zone 10 are 43° C. and 20 psia. Zone 10 represents a conventional extractive distillation column having 40 theoretical stages The product propylene oxide which is recovered via line 12 is characterized by high purity and substantially complete separate removal of impurities which were previously associated with the impure propylene oxide. The quality of this product is substantially superior to that which is obtained by conventional separation procedures.

A mixture of solvent and heavier hydrocarbon impurities is removed from zone 10 via line 13 and passed to stripper 14. Bottoms conditions in zone 10 are 139° C. and 29 psia.

In zone 14 the heavier hydrocarbon impurities, illustratively $C_6$ impurities, are stripped form the octane solvent and are removed overhead via line 15 in amount of 1.16 lbs./hr. The purified solvent returns via line 7 to extractive distillation zones 6 and 10 for further use.

What is claimed:

1. A process for the purification of crude $C_2$-$C_4$ alkylene oxides prepared by reaction of $C_2$-$C_4$ olefin and tertiary butyl hydroperoxide and containing by weight at least 1500 ppm methanol, at least 10 ppm methyl formate, at least 150 ppm propionaldehyde, at least 3000 ppm acetone, and up to 1000 ppm tertiary butyl alcohol which comprises:

(a) subjecting the said crude alkylene oxide to fractional distillation in order to separate the bulk of the higher and lower boiling impurities from partially purified alkylene oxide;

(b) passing the partially purified alkylene oxide to an extractive distillation zone and in said zone separating impurities overhead from said alkylene oxide by extractive distillation with an extractive distillation solvent;

(c) passing the alkylene oxide from step (b) to a further extractive distillation zone and in said further zone separating said alkylene oxide overhead by extractive distillation from impurities and extractive distillation solvent; and (d) distilling impurities overhead from the said solvent and returning said solvent to the extractive distillation steps (b) and (c).

2. A process for the purification of crude $C_2$-$C_4$ alkylene oxides prepared by reaction of $C_2$-$C_4$ olefin and tertiary butyl hydroperoxide and containing by weight at least 1500 ppm propionaldehyde, at least 3000 ppm acetone, and up to 1000 ppm tertiary butyl alcohol which comprises:

(a) subjecting the said crude alkylene oxide to fractional distillation in order to separate the bulk of the higher and lower boiling impurities from partially purified alkylene oxide;

(b) passing the partially purified alkylene oxide to an extractive distillation zone and in said zone removing normally heavier impurities overhead from a mixture of said alkylene oxide and extractive solvent;

(c) passing the alkylene oxide and solvent mixture to a further extractive distillation zone and in said further zone separating purified alkylene oxide overhead from a bottoms stream comprising extractive solvent and impurities; and (d) stripping said impurities overhead from the said solvent and returning said solvent to the extractive distillation steps (b) and (c).

3. The method of claim 2 wherein said alkylene oxide is propylene oxide and said extractive solvent is octane.

4. The method of claim 2 wherein said alkylene oxide is propylene oxide and said extractive solvent is a lower alkylene glycol.

* * * * *